United States Patent [19]

Thomas et al.

[11] 4,303,828
[45] Dec. 1, 1981

[54] DISINFECTOR UNIT WITH SWING-OUT TRAY

[75] Inventors: Michael D. Thomas; Francis E. Ryder, both of Arab, Ala.

[73] Assignee: Ryder International Corporation, Arab, Ala.

[21] Appl. No.: 33,469

[22] Filed: Apr. 26, 1979

[51] Int. Cl.³ .............................................. A61L 2/04
[52] U.S. Cl. ................... 219/521; 219/386; 422/307
[58] Field of Search .................. 219/521, 385–387, 219/390, 391, 399, 408, 433, 214, 218; 99/339, 371, 385, 393, 399; 34/201–202; 312/236; 422/300, 307; 126/275 E, 340

[56] References Cited

U.S. PATENT DOCUMENTS

| 366,733 | 7/1887 | Millett | 126/340 |
|---|---|---|---|
| 649,135 | 5/1900 | Millett | 126/340 |
| 745,574 | 12/1903 | Craig | 312/300 |
| 857,076 | 6/1907 | Kraus | 312/300 |
| 1,511,269 | 10/1924 | Decker | 219/218 |
| 1,597,187 | 8/1926 | Garman | 219/399 |
| 2,761,053 | 8/1956 | Schneider | 219/392 |
| 3,801,278 | 4/1974 | Wagner et al. | 219/430 |
| 4,044,226 | 8/1977 | Kadlecik | 219/521 |

Primary Examiner—Gene Z. Rubinson
Assistant Examiner—Bernard Roskoski
Attorney, Agent, or Firm—Trexler, Bushnell & Wolters, Ltd.

[57] ABSTRACT

There is disclosed a contact lens disinfector unit for sterilizing contact lenses contained within a lens case. The disinfector unit includes a housing, a heating block within the housing for heating the lens case and the contact lenses therein to a sterilizing temperature, and a tray pivotally mounted to the housing. The tray includes a lens case receiving opening adapted to receive and support the lens case. The tray is arranged to pivot or swing between an open position disposing the opening outside of the housing to permit a lens case to be placed therein, and a closed position disposing the opening above and adjacent to the heating block within the housing to bring the lens case into heat transfer contact with the heating block. The disclosed embodiment also includes a latch for releasably locking the tray in the closed position, which latch will co-act with the tray to urge the tray towards the open position after disengagement of said latch.

12 Claims, 8 Drawing Figures

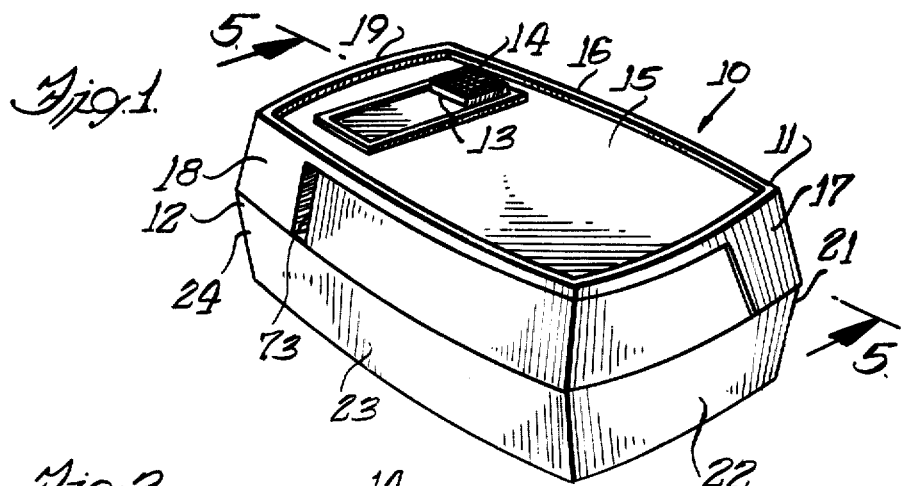
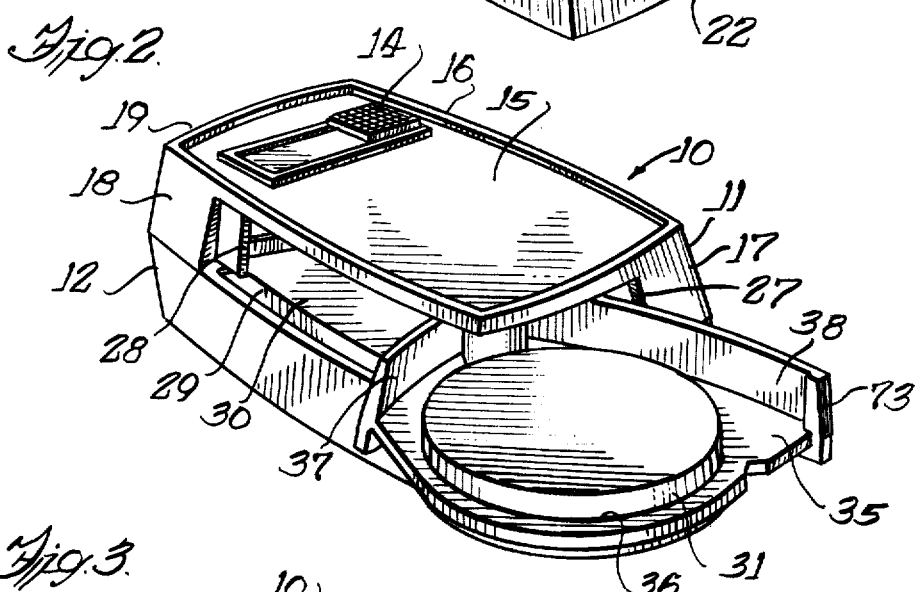
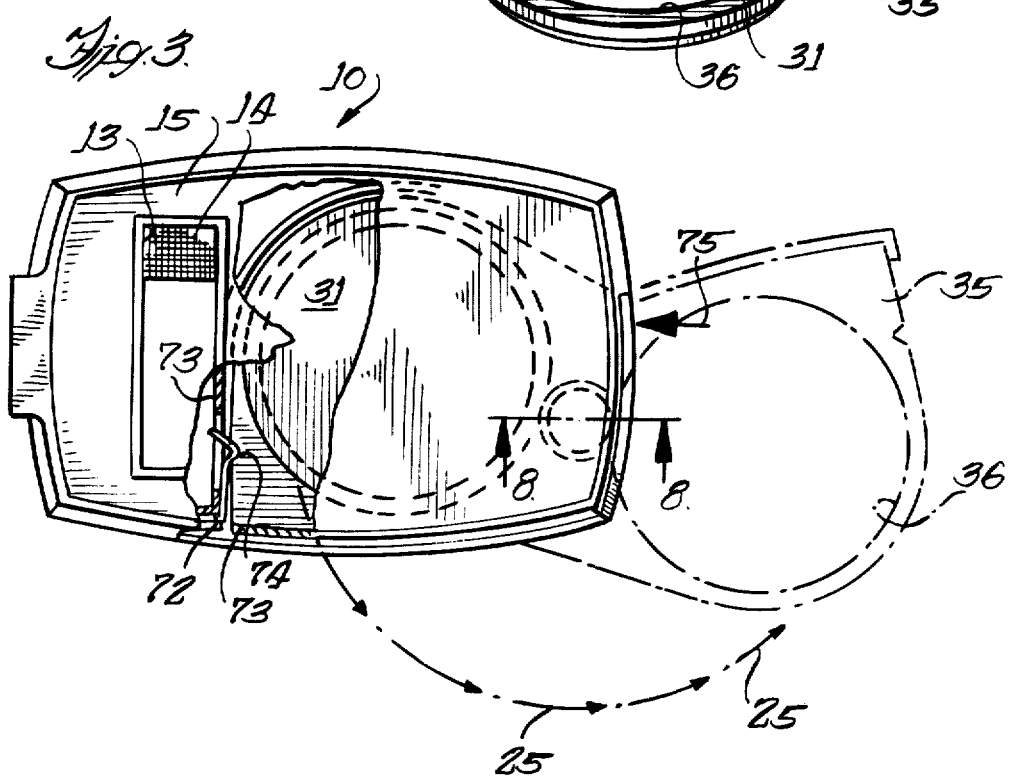

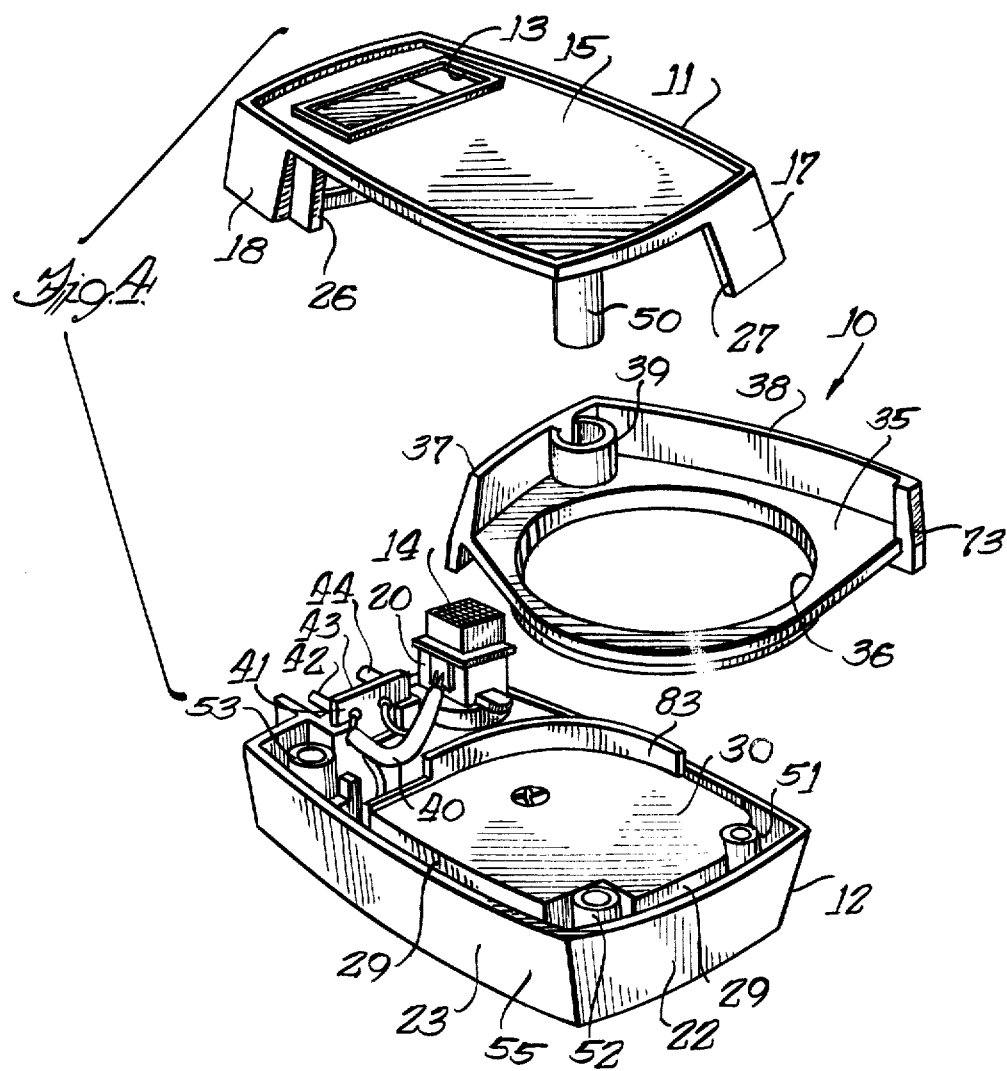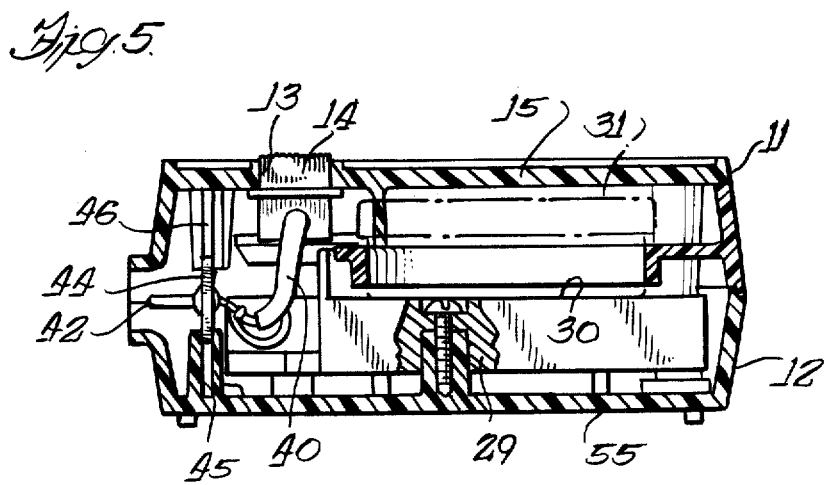

DISINFECTOR UNIT WITH SWING-OUT TRAY

BACKGROUND OF THE INVENTION

The present invention is directed generally to a contact lens disinfector unit, and more particularly to a disinfector unit which includes an improved unit design by which a lens case containing the contact lenses may be brought into heat exchange relationship with the heating block of the disinfector unit.

Contact lenses, both of the hard and soft type, often must be sterilized before they are suitble for use. To this end, each pair of contact lenses is inserted into a separate container or lens case which may also have receptacles therein for holding the right and left lenses spaced apart so they do not become confused. These containers are commonly referred to as lens cases. A quantity of disinfecting liquid is then administered to the lens case and the case is placed in engagement with a heating block for heating the liquid to a temperature sufficient to destroy harmful bacteria. After the disinfecting temperature has been reached and maintained for a sufficient period of time, the lens case and the contact lenses contained therein are permitted to cool to enable removal of the lenses and insertion upon the eye of a wearer.

Contact lens disinfector units of the prior art have been of varied design and have generally included a hinged cover and a contact lens case receiving recess having a bottom surface formed by the heating block. In order to place a contact lens case into such a disinfector unit, it is first necessary to lift the hinged cover to expose the lens case receiving recess, place the lens case into the recess to cause the bottom of the case to engage the top surface of the heating block, and then close the hinged cover. For removing the lens case from the disinfector unit, it is necessary to lift the hinged cover, manually grab the lens case, and then reclose the hinged cover. While disinfector units of this variety have proved to be generally successful, the hinged cover arrangement of these disinfector units have not maximized the convenience to the user.

From the foregoing, it can be seen that there is a need in the art for a new and improved contact lens disinfector unit which is more convenient to use. More specifically, the disinfector unit of the present invention is designed to allow the contact lens case to be removed from engagement with the heating block of the disinfector unit without requiring that the lens case be touched. To this end, the lens case is displaced from the environment of the heating block to a position externally of the unit to facilitate rapid cooling of the lens case and associated lenses before removal of the lenses from the case.

It is therefore a general object of the present invention to provide a new and improved contact lens disinfector unit design wherein the contact lens case may be displaced from engagement with the heating block without being touched.

It is a further object of the present invention to provide a new and improved contact lens disinfector unit which includes a swinging tray and a novel pivotally mounting structure which adapts the tray to swing between a first position for bringing the contact lens case into heat exchange relation with the heating block and a second position for displacing the contact lens case from the heating block and disinfector unit, while maintaining the tray in assembled, captive relation with the housing.

It is a still further object of the present invention to provide such a contact lens disinfector unit which further includes a means for assisting or urging the swinging tray towards its open position to assure that the contact lens case will be displaced from the heating block without having to be touched by the operator.

The invention therefore provides a disinfector unit for contact lenses contained within a lens case, wherein the unit includes a housing, a heating block within the housing for heating the lens case and contact lenses therein to a specified temperature, and tray means having a lens case receiving opening to receive and support the lens case. The tray means is pivotally mounted to the housing and arranged to swing between an open position disposing the opening outside of the housing to permit a lens case to be placed therein, and a closed position disposing the opening adjacent to the heating block within the housing to bring the lens case into heat transfer relation with the heating block.

BRIEF DESCRIPTION OF THE DRAWINGS

The invention, together with further objects and advantages thereof, may best be understood by making reference to the following description taken in conjunction with the accompanying drawings, in the several figures of which like reference numerals identify identical elements, and wherein:

FIG. 1 is a perspective view of a contact lens disinfector unit constructed in accordance with the present invention;

FIG. 2 is a perspective view of the disinfector unit of FIG. 1 illustrating the operation of the pivotally mounted tray to the open position with a lens case disposed therein;

FIG. 3 is a top plan view, with portions cut away, illustrating the swinging tray in the closed position;

FIG. 4 is an exploded perspective view of the disinfector unit of FIG. 1 illustrating its major component parts including a top section, a bottom section, and the swinging tray prior to assembly;

FIG. 5 is a sectional side view of the disinfector unit of FIG. 1 taken along the line 5—5 of FIG. 1;

DESCRIPTION OF THE PREFERRED EMBODIMENT

Figure 6:
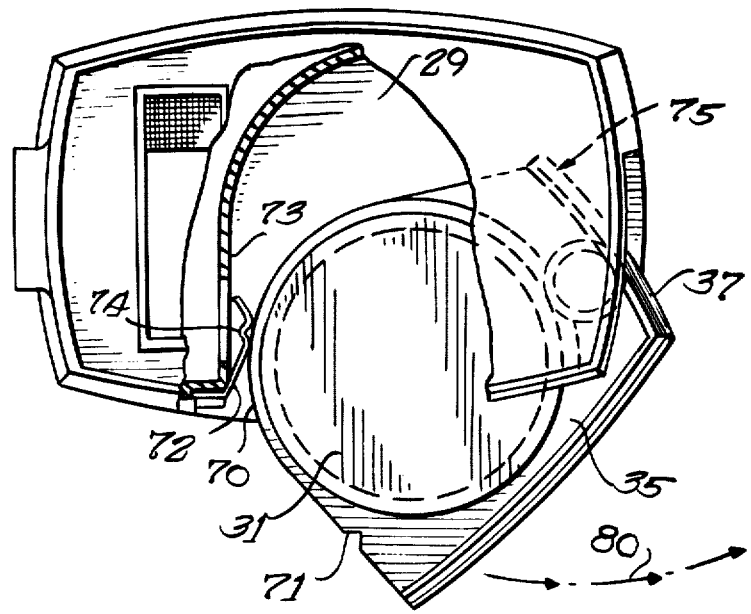
FIG. 6 is a top plan view with portions cut away illustrating the operation of the releasable latch for the swinging tray of the disinfector unit and its operation to assist in the opening of the tray in accordance with a feature of the invention.

Referring now initially to FIGS. 1 through 4, the disinfector unit thereshown is designated generally 10, and includes a housing comprised of a top section 11 and a bottom section 12. The top section 11 includes a top wall 15 and a plurality of side walls 16, 17, 18 and 19. Within the top wall 15 there is provided an opening 13 through which an actuator button 14 extends, which button is mechanically coupled to a thermal couple switch 20 (FIG. 4). The button 14, when depressed supplies power to the heating element of the unit and initiates a disinfecting cycle. Associated with the button 14 is an internal light bulb which causes the button to glow when the thermal couple switch 20 is closed, thus indicating that the unit 10 is in the heating mode.

The bottom section housing section 12 is generally dish-shaped and, as noted in FIG. 1, includes a plurality of side walls 21, 22, 23 and 24. The top section 11 and bottom section 12 and the respective side walls of each section are arranged to interfit together to as to form the housing over the outer casing of the disinfector unit 10.

As is best seen in FIGS. 2 and 4, the adjoining side walls 17 and 18 of the housing top section 11 are provided with openings or apertures 27 and 28 which are also adjoined. The openings 27 and 28 provide an access slot to the interior of the disinfector unit 10, and accommodates a lens case support tray 35. Within the bottom section 12 of the disinfector unit housing there is provided a heating block 29 which has a top surface 30 and is associated with a resistive type heater element (not shown) of conventional design. The top surface 30 of the heating block 29 is arranged to engage and support the bottom surface of a contact lens case 31 as the lens case 31; FIG. 2, which is received into the interior of the housing along with the tray 35, and is brought into heat conducting relationship with said heater block 29.

The lens case receiving tray 35 is pivotally mounted between the top housing section 11 and the bottom section 12. The tray 35 is provided with an opening 36 dimensioned for receiving and supporting the contact lens case 31. The tray 35 is pivotally mounted in a manner to be described in greater detail hereinafter with respect to FIG. 8. As can be noted from FIG. 2, the tray 35 includes side wall portions 37 and 38. The side walls 37 and 38 of the tray 35 are arranged to correspond to the openings 27 and 28 respectively in the top section 11. Accordingly, when the tray 35 is swung into its closed position, FIG. 1, the side walls 37 and 38 fill or cover the openings 27 and 28, preventing access to the interior of the unit.

As can be seen from FIGS. 2 and 3, the tray 35 is arranged to swing between a first or closed position wherein it is disposed entirely within the housing, and a second or open position as shown in FIG. 2. The movement of the tray 35 is indicated by the arrows 25. When in the open position, the tray opening 36 is disposed entirely outside of the disinfector unit housing to facilitate the removal of a lens case 31, or alternately, the placing of the contact lens case 31 therein. As the tray 35 is swung into its closed position, the opening 36 will be disposed adjacent to the upper surface 30 of the heating block 29 so that the bottom surface of the lens case 31 will rest upon and engage the heating block surface 30 in heat exchanging relationship.

As can be appreciated from the foregoing, the tray 35 can be moved between its closed and open positions by an operator without the operator having to touch the lens case 31. Accordingly, after a disinfecting cycle has been completed, should the contact lens case 31 still be hot, the operator need only push the tray to the open position, which will facilitate rapid cooling. As such, there is no need to handle the lens case in order to displace or remove it from engagement with the heating block 29. Thus, a potential source of injury to an operator or user is minimized.

Referring now to FIGS. 4 and 5, the disinfector unit 10 is thereshown with its top section 11, bottom section 12, and contact lens case receiving tray 35 in exploded relation so as to render visible the interior of the disinfector unit 10. Basically, the disinfector unit 10 includes the aforementioned heating block 29 and the thermal couple switch 20 which is disposed beneath the button 14, which button, as previously explained, is received in the opening 13 within the top wall 15 upon assembly. A power supply circuit 40 includes a resistor heating element (not shown) and is adapted to be connected to an electric power source by a connector 43. The connector 43 is formed from a phenolic board 41 and includes a pair of connector pins 42 and 44. The board is received within a pair of slots 45 formed in the bottom section 12 and a corresponding pair of slots 46 formed in the top section 11. The slots 45 and 46 are arranged to be in alignment upon assembly of the sections 11 and 12 so as to hold the connector 43 firmly in place. The pins 42 and 44 are, of course, arranged to interconnect with a power cord for ultimate connection to a power receptacle.

The power supply circuit 40 and resistive heating element combine to heat the heating block 29 to a temperature which has been determined to be sufficient to achieve disinfecting of the lenses. The heating block 29 is in contact with the resistive heating element mentioned above, and due to the surface-to-surface contact with the lens case 31 during the disinfecting cycle, applies heat evenly thereto for sufficient period of time so as to raise the temperature of the disinfecting solution to that required to destroy harmful bacterial on the lenses. The circuit means providing power to the resistive heater is of a type well-known in the art and it is deemed unnecessary that it be described in detail herein.

The structural features which permit assembly will now be considered. In this regard, the top section 11 and bottom section 12 are provided with a plurality of cylindrical post members, post members 51, 52, and 53 for the bottom section being illustrated in FIG. 4, along with post member 50 for the top section. Each of the cylindrical post members 51, 52 and 53 of the bottom section 12 finds a corresponding cylindrical member in the top cover section 11 although only the post member 50 which aligns with bottom section post 52 is visible. The cylindrical post members are integrally formed with their respective sections 11 and 12 and are positioned to be engaged in aligned relation upon assembly of the sterilizer unit sections 11 and 12. Each of the cylindrical members 51 through 53 includes an internal through bore which is arranged to receive a threaded fastener 61, FIG. 8; correspondingly, the post members on the upper housing section 11 include a blind bore. The fasteners 61 employed are self-tapping and serve to draw and maintain the respective sections 11 and 12 into assembled relation.

Figure 8:
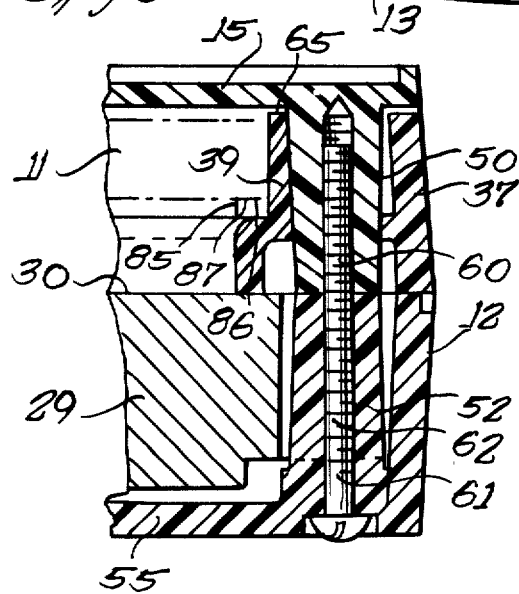
FIG. 8 is a partial cross sectional view taken generally along lines 8—8 of FIG. 3 illustrating the pivotal connection of the tray to the housing.

The tray 35, in addition to having the opening 36 and side walls 37 and 38, also includes an apertured boss structure 39 taking the form of a hollow cylinder. As discussed above, the tray 35 is mounted for pivotal movement with respect to the assembled housing sections 11 and 12. The preferred manner of effecting this pivotal mounting is shown in FIG. 8. In this regard, the cylindrical post member 52 of bottom section 12 extends from the bottom wall 55 towards top section 11 and terminates proximate to the upper edge surface of the adjacent side walls 22 and 23. The cylindrical post member 50 of the top section 11 similarly is integrally formed with said top section, and extends towards and is in aligned relation with the cylindrical post member 52. As a result, the bores 60 and 62 of said post members 50 and 52 are aligned with the threaded screw 61 maintained aligned assembled relation.

The diameter of the aperture in the boss 39 of the tray 35 is sized to receive the cylindrical post member 50, such that the tray 35 is free to pivot thereabout. As can be seen in FIG. 8, the cylindrical member 50 is only of slightly greater axial length than the boss 39. As a result, when the housing sections 11 and 12 are assembled, a slight clearance 65 will exist between the boss 39 and side walls 37 and 38 of the tray 35 and the top wall 15 of section 11. As such, the design of the present invention assures free pivotal movement of the tray 35 subsequent to the secure assembly of the housing sections 11 and 12, yet confine the tray to permit lateral and longitudinal movement. As can be noted from the foregoing, by this arrangement, the tray is maintained in a captive pivotal assembly, yet binding engagement of the tray with the housing section side walls is precluded, notwithstanding the secure assembly of the unit. There thus is provided a simple, yet effective manner of pivotally mounting the tray 35, which is achieved with a minimum of structural features and assembly time.

Referring now to FIG. 6, it can be seen that the tray 35 also includes a curved peripheral surface portion 70 with a notch 71 formed therein. A leaf spring-type latch 72 is mounted to an inner wall 73 of the top section 11 and is arranged to urge against the peripheral surface of the tray 35. The spring 72 has a bifurcated end portion 74 which is structured to be received within the notch 71 when the tray 35 is in its closed position, as shown in FIG. 3. Hence, when the tray 35 is swung to said closed position, it will be releasably locked in that position, by the engagement of end portion 74 in notch 71.

In order to move the tray 35 and swing it towards its second position, externally of the housing, two procedures are available. First, when the tray 35 is in the closed position, FIG. 1 or 3, the vertical edge 73 of the tray side wall 38 will be spaced from the corresponding portion of the side wall 18 of housing section 11. As such, this is provided a slight opening, which permits the operator to grasp the tray and commence pivotal movement. As an alternate method, it should be noted that the position of the post members 50 and 52 is such that they are disposed intermediate their respective side walls 17 and 22. Accordingly, opening of the tray can be effected by the application of force to the tray side wall 37 at a point remote from the pivot location, as indicated by arrow 75. The application of force to the tray will overcome the releasable locking effect of the leaf spring 72 and will cause the latch formed by the spring 72 and notch 71 to disengage. After disengagement of the latch, the spring 72 will remain in contact with the peripheral surface 70 of the tray 35 and once the tray has reached the position shown in FIG. 6, the spring 72 will act upon the curved peripheral surface 70 to urge the tray 35 towards its open position as indicated by the arrows 80. The spring 72 will assure that the tray 35 is open to a substantially fully opened position whereupon further opening to a position wherein the case 31 is clear of the housing may be easily obtained by an operator. In the open position, of course, the lens case 31 will be displaced from the heating block 29 and can be removed immediately, or allowed to cool for a period of time before complete removal from the tray 35.

Figure 7:
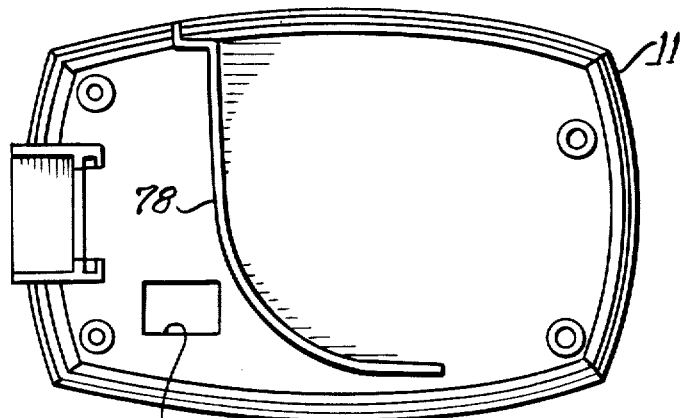
FIG. 7 is a plan view of the underside of the housing top section of the disinfector unit.

Referring now to FIG. 7, it can be seen that the top section 11 of the disinfector unit housing includes the curved wall section 78. Also, by making reference to FIG. 4, it can be noted that the heating block 29 also has a curved wall portion 83 which extends from its upper surface 30. The wall portions 78 and 83 are arranged to be in alignment upon assembly of the top section 11 and bottom section 12 and to engage upon assembly. As a result, the power supply circuit 40 and its internal elements including the thermal couple switch 20 are completely enclosed even when the tray 35 is in its opened position. Hence, access to the power supply circuitry is precluded, affording an important safety advantage.

Lastly, it can be noted from FIGS. 5 and 8, that when the contact lens case 31 rests upon the upper surface 30 of the heating block 29, there exists a slight space 85 between the upper peripheral surface 86 of the tray opening 36 and a bottom peripheral surface 87 of the lens case 31. As a result of this space 85, it is assured that the lens case will make broad and complete surface contact with the heating block 29 to achieve maximum and uniform heat exchange between the lens case and heating block.

From the foregoing, it can be seen that the present invention provides a new and improved contact lens disinfector unit. The disinfector unit of the present invention includes a new and improved arrangement for receiving a contact lens case and bringing the contact lens case into heat exchange relation with the heating block. The arrangement includes the swinging tray which is pivotally mounted to the housing and which is arranged to swing between an open position to allow a contact lens case to be placed therein and a closed position for disposing the contact lens case against the heating block in heat exchange relation. The present invention further provides a releasable latch for releasably locking the swinging tray in its closed position and which latch provides an additional function of urging the tray towards its open position after being disengaged. As a result of the foregoing, a disinfector unit has been provided by the present invention which negates the need for an operator to manually touch the contact lens case for displacing the same from the heating block to effect cooling thereof to the ultimate end of increasing the convenience in using the disinfector unit and precluding possible injury to the user.

While a particular embodiment of the present invention has been shown and described, modifications may be made, and it is therefore intended to cover in the appended claims all such changes and modifications which fall within the true spirit and scope of the invention, as defined by said claims.

The invention is claimed as follows:

1. A contact lens disinfector unit for sterilizing contact lenses immersed within a disinfecting solution contained within a lens case, said disinfector unit comprising: a housing including a plurality of side walls and top and bottom wall structure, wherein said side walls of said housing define an opening intermediate said top and bottom wall structure; electrical heating means disposed within said housing for heating a lens case, contact lenses and disinfecting solution to an asepticizing temperature, said heating means including an electrically heated heating block having a generally planar upper surface; and tray means including a through aperture; a lens case disposed in said aperture with a base portion of said lens case exposed for engagement with said heater block upper surface; said tray means being pivotally mounted to said housing proximate said opening provided in said side walls, for swinging movement between an open position wherein said lens case receiving aperture is disposed exteriorly of said housing to permit reception and removal of the lens case therefrom as necessary, and a closed position wherein said tray means is received within said housing through said side wall opening to dispose the lens case carried by said tray means in heat transfer contact with said planar upper surface of the heater block, and said tray means including peripheral wall structure arranged to close said housing side wall opening when said tray means is in the closed position.

2. A disinfector unit as defined in claim 1 wherein said housing further includes a bottom section which houses said heating block and a top section into which said tray means is adapted to swing and wherein said top section includes said adjacent sides having said adjoining openings.

3. A disinfector unit as defined in claim 1 further comprising latch means for releasably locking said tray means in said closed position.

4. A disinfector unit as defined in claim 3 wherein said latch means includes a notch carried by said tray means and a leaf spring within said housing, said leaf spring having an end portion arranged to resiliently enter said notch when said tray means is in said closed position.

5. A disinfector unit as defined in claim 3 wherein said latch means includes a spring member and said tray includes a peripheral surface portion arranged to be acted upon by said leaf spring such that upon movement of the tray from the latched position, said spring will urge said tray means towards said open position.

6. A disinfector unit as defined in claim 5 wherein said peripheral surface portion includes a curved surface portion.

7. A disinfector unit as defined in claim 1 wherein said housing includes a bottom section and a top section, said bottom section houses said heating block, and wherein said unit further includes mounting means for pivotally mounting said tray means comprising a first cylindrical member extending from said top wall and a hollow integral boss member formed in said tray means, said hollow boss member including a through bore which receives said cylindrical member to affix said tray means to said housing while mounting said tray means for swinging movement about said first cylindrical member.

8. A disinfector unit as defined in claim 7 wherein said bottom section includes a second cylindrical member extending toward said first cylindrical member and arranged for aligned engagement with said first cylindrical member upon assembly of said sections, wherein said first and second cylindrical members each include a bore for receiving a fastener to enable secure assembly of said sections, and wherein said first cylindrical member is longer in axial dimension than said tray means hollow boss member so that upon assembly of said sections, as said first and second cylindrical members are drawn together into secure relation, while said tray means remains free to pivot about said first cylindrical member.

9. A disinfector unit according to claim 1, further including a barrier means disposed within said housing proximate the periphery of said heater block upper surface, said barrier means preventing access to said electrical heating means through the adjoining side wall openings when said tray means is in the open position, and functioning as a stop for said tray means by movement thereof to said closed position.

10. A contact lens disinfector unit for sterilizing contact lenses immersed within a disinfecting solution contained within a lens case, said disinfector unit comprising: a housing including top and bottom sections and having a plurality of side walls, wherein a pair of adjacent side walls of said housing include adjoining openings; electrical heating means disposed within said housing for heating a lens case, contact lenses and disinfecting solution to an asepticizing temperature, said heating means including an electrically heated heating block having a generally planar upper surface; and tray means including a through aperture; a lens case disposed in said aperture with a base portion of said lens case exposed for engagement with said heater block upper surface; said tray means being pivotally mounted to said housing proximate the openings provided in adjacent side walls thereof, for swinging movement between an open position wherein said lens case receiving aperture is disposed exteriorly of said housing to permit reception and removal of the lens case therefrom, as necessary, and a closed position wherein said tray means is received within said housing through said adjoining side wall openings to dispose the lens case carried by said tray means in heat transfer contact with said planar upper surface of the heater block, and said tray means including a pair of adjacent peripheral side wall portions arranged to close said housing side wall openings when said tray means is in the closed position.

11. A disinfector unit according to claim 10, wherein said tray is pivotally mounted at a location intermediate one of the side wall portions thereof, such that when in the closed position either of said wall portions may be engaged to cause said tray to swing to the open position.

12. A disinfector unit according to claim 10 further including means to effect said pivotal mounting of said tray, said means comprising an annular base formed on said tray and defining a through bore, a first cylindrical projection formed on said top section and a second cylindrical projection formed on said bottom section, with said projection being disposed in aligned, abutting engagement upon assembly of said sections, said first projection being disposed in said bore, with said annular boss and said bore serving to maintain said tray in captive pivotal disposition with respect to said assembled housing sections.

* * * * *